US006869218B2

(12) United States Patent
Winsor

(10) Patent No.: US 6,869,218 B2
(45) Date of Patent: Mar. 22, 2005

(54) SELF DIAGNOSTIC SYSTEM FOR OPTICALLY COUPLED DIGITAL RADIOGRAPHY

(75) Inventor: Robin Winsor, Calgary (CA)

(73) Assignee: Imaging Dynamics Company Ltd., Calgary (CA)

( * ) Notice: Subject to any disclaimer, the term of this patent is extended or adjusted under 35 U.S.C. 154(b) by 106 days.

(21) Appl. No.: 10/302,820

(22) Filed: Nov. 25, 2002

(65) Prior Publication Data

US 2003/0118152 A1 Jun. 26, 2003

Related U.S. Application Data

(60) Provisional application No. 60/333,207, filed on Nov. 23, 2001, provisional application No. 60/333,224, filed on Nov. 23, 2001, provisional application No. 60/333,206, filed on Nov. 23, 2001, and provisional application No. 60/333,252, filed on Nov. 23, 2001.

(51) Int. Cl.[7] .............................................. G01D 18/00
(52) U.S. Cl. ........................ 378/207; 378/63; 378/206; 250/252.1; 250/370.11
(58) Field of Search .............................. 378/19, 63, 65, 378/98.3, 98.8, 205, 206, 207, 98.12; 250/252.1, 367, 368, 369, 370.11, 372, 370.09

(56) References Cited

U.S. PATENT DOCUMENTS 5,235,191 A * 8/1993 Miller ..................... 250/486.1
5,905,772 A * 5/1999 Rutten et al. ............... 378/98.8
6,260,999 B1 * 7/2001 Wofford et al. ............. 378/205
6,478,462 B2 * 11/2002 Polkus et al. ............... 378/207
6,600,159 B2 * 7/2003 Overdick et al. ...... 250/370.11
2004/0022352 A1 * 2/2004 Suzuki ......................... 378/19
2004/0022363 A1 * 2/2004 Ghelmansarai ............. 378/206

* cited by examiner

Primary Examiner—Allen C. Ho
(74) Attorney, Agent, or Firm—D. Doak Horne; Cowling Lafleur Henderson LLP

(57) ABSTRACT

This invention relates to a self diagnostic apparatus for a radiographic imaging system. The system includes a radiographic source and a camera, and the apparatus comprises: a scintillator positioned between the optical pathway of the radiographic source and the camera, and made of a material which fluoresces when struck by x-rays, including one in the group of terbium doped gadollineum oxysulfide or thallium doped cesium iodide; a resolution target located at the periphery of the scintillator and made of a material that passes at least shortwave ultraviolet light; an ultraviolet source positioned in line of sight of the scintillator and target; and, a control system for capturing a self-diagnostic reference image by activating the ultraviolet source, and activating the camera to take an image created by the visible light emitted by the scintillator material when illuminated by the UV light. A short wavelength UV light for example 254 nm excites the scintillator material to emit light from which can then be captured an image of the resolution targets.

20 Claims, 3 Drawing Sheets

SELF DIAGNOSTIC SYSTEM FOR OPTICALLY COUPLED DIGITAL RADIOGRAPHY

RELATED APPLICATIONS

This application incorporates by reference all subject matter set out in related U.S. provisional application No. 60/333,207 entitled "Positioning Stand for a Radiography Imaging Device", No. 60/333,224 entitled "Lens Assembly and Barrel Correction Method for X-Ray System", and No. 60/333,206 entitled "Balancing Areas of Varying Density in a Digital Image", and the regularized U.S. patent applications therefor each filed Nov. 23, 2001, as well as the subject matter contained in U.S. provisional application No. 60/333,252 entitled "Self-Diagnostic System for Optically Coupled Digital Radiography".

FIELD OF THE INVENTION

The present invention is directed generally to an apparatus and method for use in the field of digital radiography, and in particular to a method and apparatus whereby an optically coupled digital radiography system may perform a self diagnostic to ensure that all components are working correctly without requiring an external radiation source.

BACKGROUND OF THE INVENTION

For more than one hundred years photographic films have been used to capture and display X-rays for diagnostic purposes. In the last ten years or so, digital radiography has become increasingly popular. Digital radiography refers to the application of digital image processing techniques to projection radiography (x-rays). Digitally recorded x-rays are superior to those recorded with photographic film due to the greater dynamic range of the digital recording system. Furthermore, computer image processing techniques provide a wealth of capabilities to study otherwise obscured details within the image.

To take a digital radiograph, a digital radiography imaging unit is positioned behind a subject. A standard radiographic generator directs radiation through the subject to a fluorescent-imaging screen mounted just behind the front surface of the imaging unit. The imaging screen is the conversion media for radiation to visible light. The fluorescent-imaging screen absorbs the radiographic radiation and emits light of a particular wavelength, which closely matches the peak sensitivity of a charge coupled device (CCD) camera. A front-surfaced mirror is positioned at a 45-degree angle inside the imaging unit to direct the radiographic image into the CCD camera. The mirror allows the CCD camera to be positioned out of the direct path of the radiation, effectively shielding it from radiation exposure and prolonging its life. A high-efficiency lens reduces the image and directs it onto the surface of the CCD.

The visual image formed by the fluorescent-imaging screen is converted into a digital image by the CCD sensor. A control computer converts the image into a medical image file that can be viewed for clinical diagnosis, enhanced and electronically stored with the patient demographic information in a picture archiving system.

In a digital radiographic imaging system, it is often desirable to check that all components are working correctly and that no image degradation is occurring. Such degradation could arise from a multitude of sources such as a rise in electronic noise levels, mechanical shock, loss of focus, failure of cooling systems etc.

SUMMARY OF THE INVENTION

According to one aspect of the invention, there is provided a method and apparatus for obtaining a reference digital image without requiring that x-rays strike the system.

In particular, a self-diagnostic apparatus for a radiographic imaging system is provided. The system includes a radiographic source and a camera, and the self-diagnostic apparatus comprises (a) a scintillator positioned between the optical pathway of the radiographic source and the camera;

(b) a resolution target located at the periphery of the scintillator and made of a material that passes at least shortwave ultraviolet light;

(c) an ultraviolet source positioned in line of sight of the scintillator and target; and, (d) a control system for capturing a self-diagnostic reference image by activating the ultraviolet source, and activating the camera to take an image created by the visible light emitted by the scintillator material when illuminated by the UV light.

In accordance with a further aspect of the present invention there is provided a method of self-diagnostic testing for a digital radiography system, the method comprising the steps of:

illuminating a scintillator of a digital radiography system including a target area;

imaging the scintillator with a digital camera of the radiography system, including the target area to form at least one test image;

comparing the test image to a predetermined reference image; and reporting a result of the comparison.

The method and apparatus provide self-testing without using x-rays, hence without requiring an x-ray technician be present for the testing.

BRIEF DESCRIPTION OF THE DRAWINGS

The present invention will be further understood with reference to the accompanying drawings in which.

DETAILED DESCRIPTION

Figure 1:
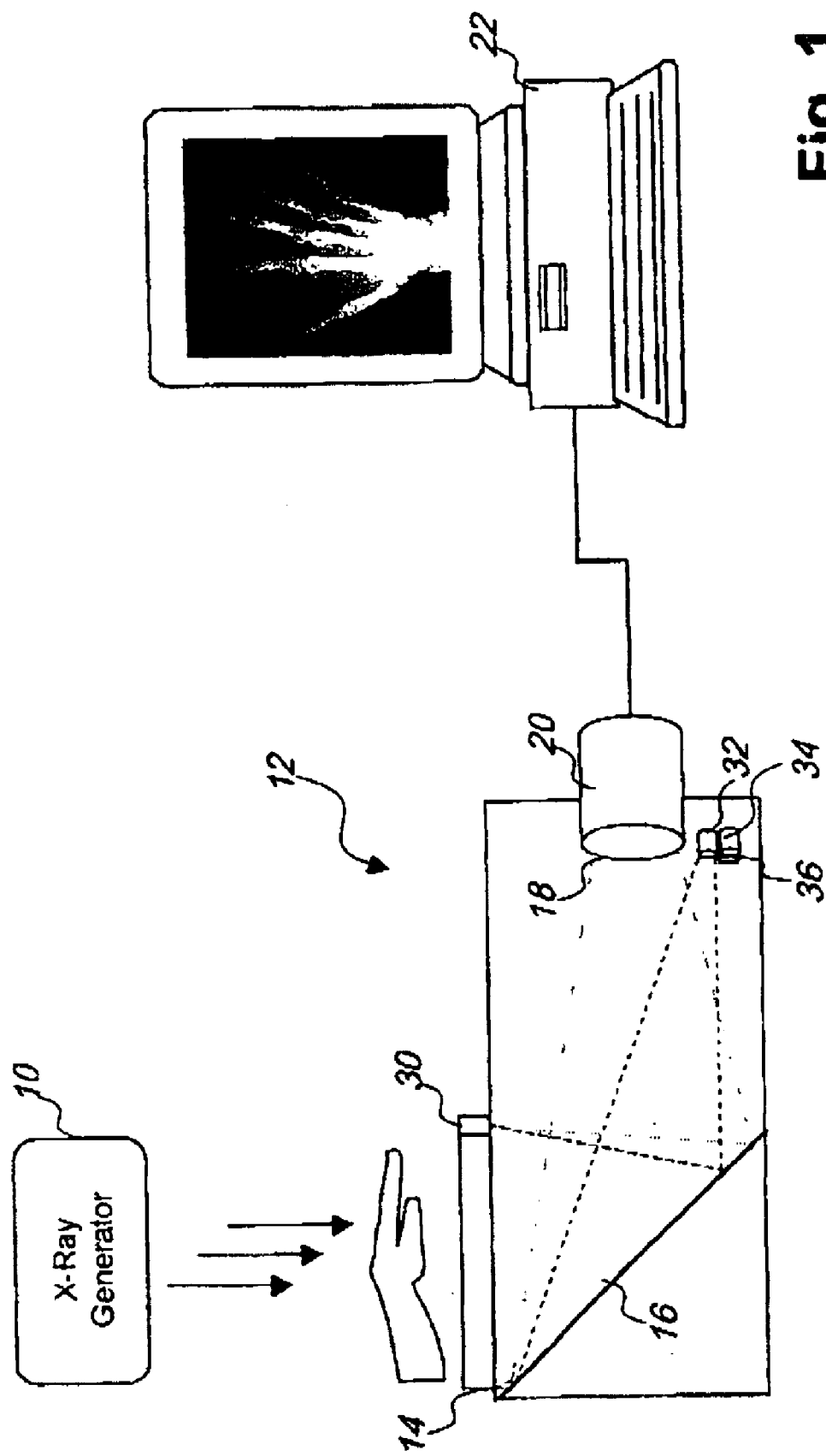
FIG. 1 schematically illustrates a self-diagnostic system for a digital radiography system having a UV light source in accordance with an embodiment of the present invention.

Referring to FIG. 1, an x-ray imaging system is provided for taking digital x-ray images of a subject, such as a patient for medical diagnostic purposes. As soon as a patient is in position and a part of the patient's body selected for imaging has been set in place, an x-ray source 10 is turned on and x-rays are directed towards the patient. X-rays passing through the patient are captured by a detector 12 and converted into a digital x-ray image. In particular, the x-ray image reaching the detector 12 is first converted into visible light by a scintillator 14. The visible light is then reflected by a mirror 16 towards lenses in a lens assembly 18, which reduces and directs the visual image onto the surface of a Charge Coupled Device (CCD) camera 20, which converts the visual image into a digital image. The digital image is then transmitted to a computer 22 for imaging processing and storage.

A self diagnostic system and method are provided for obtaining a reference digital image without requiring that x-rays strike the system. A plurality of resolution targets 30 are placed around the periphery of the scintillator in such a manner that they are on the surface of the scintillator 14 but are outside the portion which is used in diagnostic imaging of patients. These targets 30 are made of a material that passes both visible and short wave ultraviolet light, more specifically, ultraviolet light of 254 nanometer wavelength. The targets 30 may be similar to the commonly used line pair resolution targets employed in optical testing. Although the present embodiment describes the use of line pair resolution targets 30, other shapes and forms of target may also be used.

In addition to the reference targets 30, up to three lamps 32, 34, 36 are provided within the space between the scintillator and the lens. One of these lamps 32 emits visible light at a wavelength similar to the scintillator. The second lamp 34 emits ultraviolet light at 254 nm wavelength and the third lamp 36 emits ultraviolet light at 365 nm wavelength. A cost effective embodiment includes a single lamp 34 that emits short wavelength ultraviolet light, for example 254 nm.

The scintillator in digital radiography systems is made of a material which fluoresces when struck by x-rays, such as terbium doped gadollineum oxysulfide or thallium doped cesium iodide. Terbium doped gadollineum oxysulfide reacts very strongly when illuminated by short wave ultraviolet light. Thallium doped cesium iodide also reacts to the short wave light but less strongly than the gadollineum oxysulfide. Both emit light during this reaction in a similar manner to when they are struck by x-rays.

The self-diagnostic system further comprises circuitry and power supplies (not shown) to turn on and off the lamps 32, 34, 36 for short durations as required under the control of a software program being run by the computer 22.

The self-diagnostic method comprises the following steps:

A set of reference image are captured and stored when the imaging system is known to be working well. For example following factory calibration. These reference images are produced by lighting each of the three lamps 32, 34 and 36 in turn and using the CCD camera 20 to take images just as it would if an x-ray pulse had been detected. The illumination is provided either by the visible light from the lamp 32 or long wavelength ultraviolet lamp 36 or in the case of the short wavelength ultraviolet lamp 34 by the visible light being output from the scintillator reaction to the short wavelength ultraviolet light.

In diagnostic mode, new images are taken in the same manner. These are compared to the reference image. Any changes between the reference and diagnostic sets will indicate a change in system performance.

Figure 2:
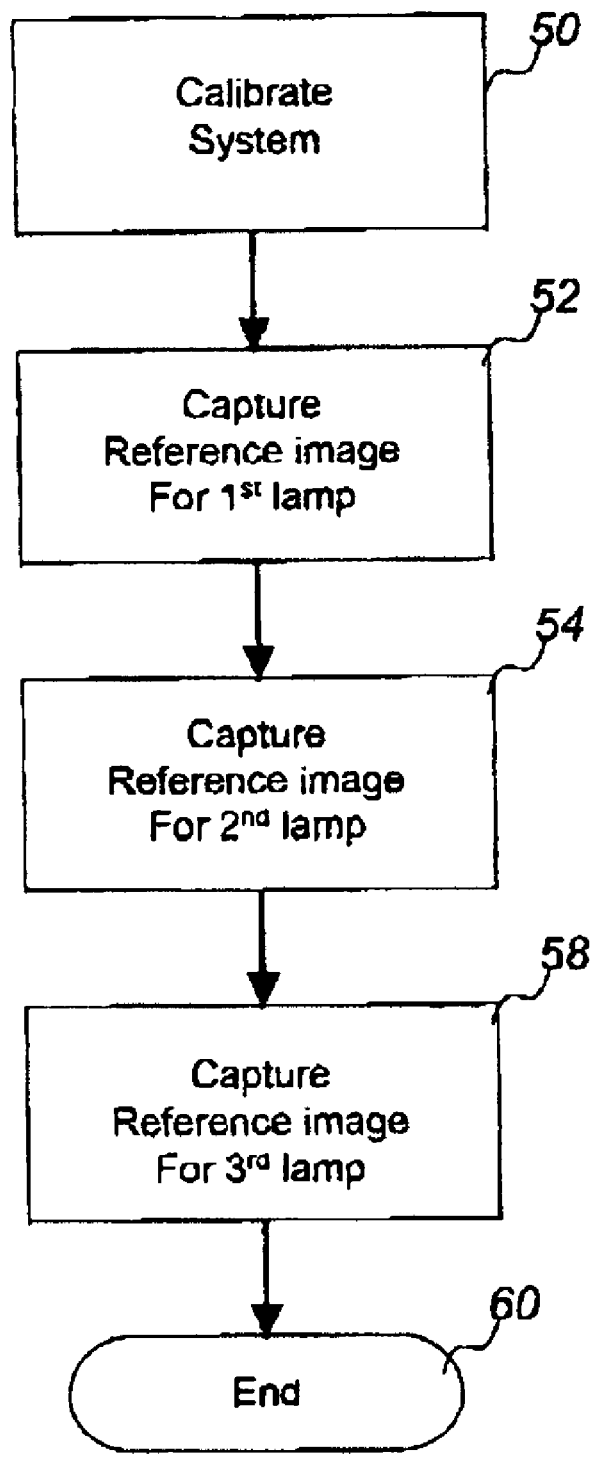
FIG. 2 illustrates in a flow chart, a method of initializing the self-diagnostic system of digital radiography system of FIG. 1, in accordance with an embodiment of the present invention.

Referring to FIG. 2, there is illustrated in a flow chart a method of initializing the self-diagnostic system of digital radiography system of FIG. 1, in accordance with an embodiment of the present invention. The self-diagnostic system of digital radiography system of FIG. 1 is first initialized as represented by a start block 50. A first reference image is captured for a first lamp, as represented by a process block 52. A second reference image is captured as represented by a process block 54, because the short wave ultraviolet lamp excites the scintillator to emit visible light. A third reference image is captured as represented by a process block 58 and the initializing is completed as represented by an end block 60. These reference images are stored in non-volatile memory for later use in self-diagnostic testing.

The single lamp version, using a short wavelength ultraviolet lamp, would only require one reference image, involving the step corresponding to process blocks 54.

Figure 3:
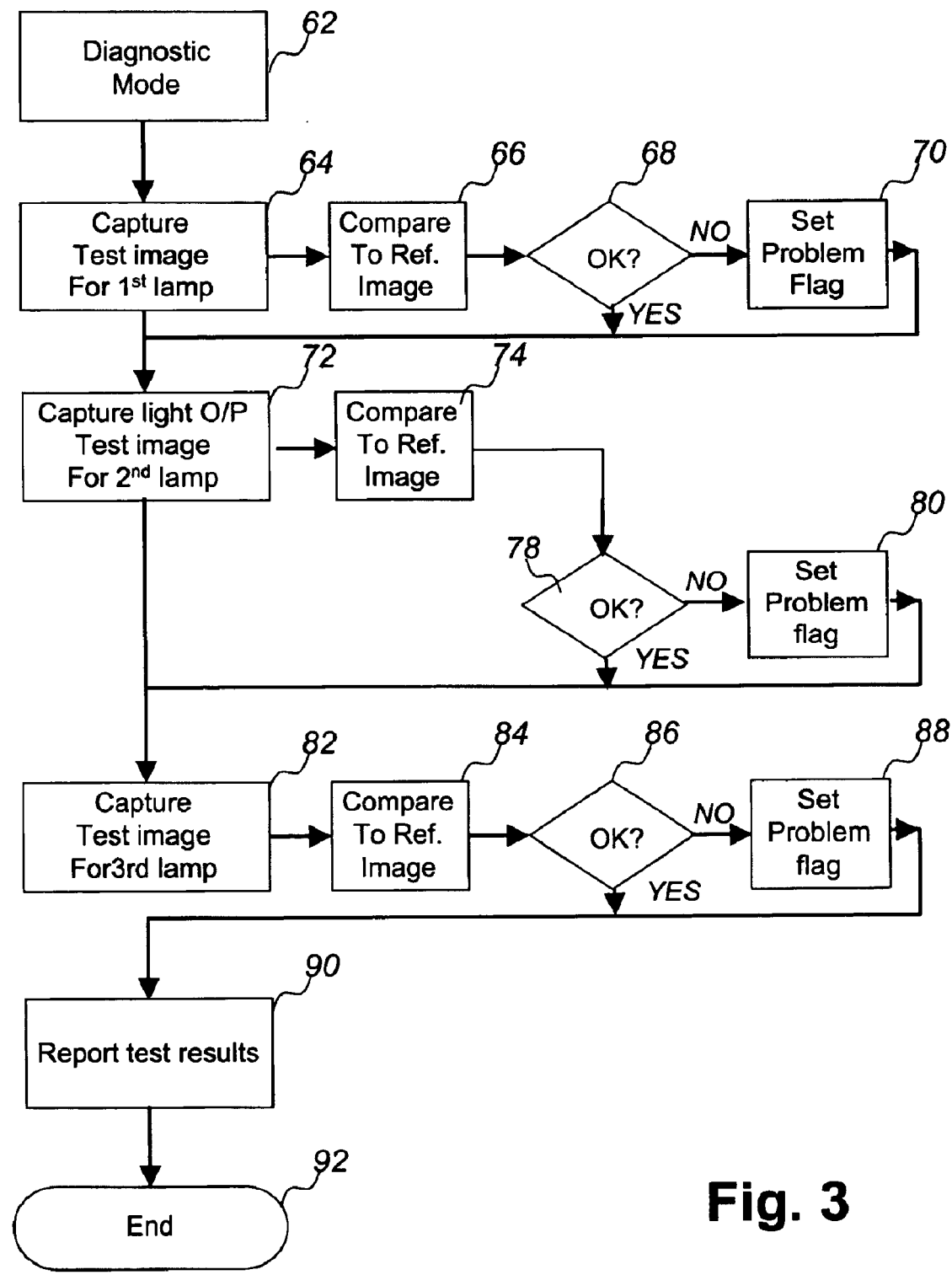
FIG. 3 illustrates in a flow chart, a method of self-diagnosing the digital radiography system of FIG. 1, in accordance with an embodiment of the present invention.

Referring to FIG. 3, there is illustrated in a flow chart a method of self-diagnosing the digital radiography system of FIG. 1, in accordance with an embodiment of the present invention. The self-diagnostic method begins as represented by a start block 62. A first test image is captured, as represented by a process block 64. The first test image is compared to the first reference image, as represented by a process block 66. If the comparison is not within acceptable parameters as represented by a decision block 68, a problem is indicated, as represented by a process block 70 and returns the method to a step of capturing a second test image for the second lamp, as represented by a process block 72. If the first comparison is acceptable, the YES path returns the method to the process block 72.

A second test image is captured, as represented by a process block 72. The second test image is compared to the second reference image, as represented by a process block 74. If the comparisons are not within acceptable parameters as represented by a decision block 78, a problem is indicated, as represented by a process block 80 and returns the method to a step of capturing a third test image for the third lamp, as represented by a process block 82. If the second comparison is acceptable, the YES path returns the method to the process block 82.

The single lamp version, using a short wavelength ultraviolet lamp, would only require one test image and light output level, involving the steps corresponding to process blocks 72, 74, 78 and 80.

A third test image is captured, as represented by a process block 82. The third test image is compared to the third reference image, as represented by a process block 84. If the comparison is not within acceptable parameters as represented by a decision block 86, a problem is indicated, as represented by a process block 88 and returns the method to a step of reporting test results, as represented by a process block 90. If the third comparison is acceptable, the YES path returns the method to the process block 90.

Once the test images are all captured and compared to the reference images, a self-diagnostic test result is generated, showing any problems that are found, as represented by the process block 90, then the self-diagnostic test ends 92. The comparison involves comparing the test image to the reference image stored as a bitmap. However more sophisticated image comparison algorithms could be used.

As the embodiment of FIG. 1 includes a computer, the report would most likely be presented on the computer using a suitable user interface, for example in conjunction with further diagnostic routines, trouble ticket generation or other reporting to radiography personnel.

Although the above embodiments describe the use of three lamps 32, 34, 36 it is also possible to use a smaller number of lamps. For example, only the short wave ultraviolet lamp 34 could be used for testing the scintillator light output and camera resolution. Alternatively, a two-lamp system could use the visible lamp 32 to test camera resolution on a regular basis and the short wave ultraviolet lamp 34 could be used for periodic testing of the scintillator output. Various other combinations of lamps and tests are also possible to provide different test parameters.

Although the above embodiments describe the use of an associated computer and software controlling the power to the lamps it is also possible to control the duration of the illumination by providing a shutter mechanism in front of the lamps such that very short pulses of light may be obtained.

In another implementation of the above method, the associated computer 22 can be programmed to perform the self-diagnostic test at predetermined times when the radiographic system is known to be idle. It may also be programmed to communicate the results of its analysis, particularly in the case of a detected problem to concerned parties such as the radiology department or the manufacturer of the device.

While the preferred embodiments of the invention have been illustrated and described, it will be appreciated that various changes can be made therein without departing from the scope of the invention as defined in the claims.

What is claimed is:

1. A self-diagnostic apparatus for a radiographic imaging system, the system including a radiographic source and a camera, the apparatus comprising
   (a) a scintillator positioned between the optical pathway of the radiographic source and the camera,
   (b) a resolution target located at the periphery of the scintillator and made of a material that passes at least short wave ultraviolet light;
   (c) an ultraviolet source positioned in line of sight of the scintillator and target; and,
   (d) a control system for capturing a self-diagnostic reference image by activating the ultraviolet source, and activating the camera to take an image created by the visible light emitted by the scintillator material when illuminated by the UV light.

2. A self-diagnostic apparatus as claimed in claim 1 wherein the ultraviolet light source is short wave ultraviolet source.

3. A self-diagnostic apparatus as claimed in claim 2 wherein the ultraviolet light source provides about 254 nm wavelength ultraviolet light.

4. A self-diagnostic apparatus as claimed in claim 1 wherein the ultraviolet light source is long wave ultraviolet source.

5. A self-diagnostic apparatus as claimed in claim 4 wherein the ultraviolet light source provides about 365 nm wavelength ultraviolet light.

6. A self-diagnostic apparatus as claimed in claim 1 further comprising a visible light source.

7. A self-diagnostic apparatus as claimed in claim 6 wherein the visible light source is for illuminating the scintillator including the resolution target.

8. A self-diagnostic apparatus as claimed in claim 1 wherein control system includes means for determining an amount of light emitted by the scintillator.

9. A self-diagnostic apparatus as claimed in claim 8 wherein means for determining includes the camera of the digital radiography system.

10. A method of self-diagnostic testing for a digital radiography system, the method comprising the steps of:
    illuminating with an ultraviolet light source a scintillator of a digital radiography system including a target area;
    imaging the scintillator with a digital camera of the radiography system, including the target area to form at least one test image;
    comparing the test image to a predetermined reference image; and
    reporting a result of the comparison.

11. A method as claimed in claim 10 wherein the ultraviolet light source is short wave ultraviolet source.

12. A method as claimed in claim 11 wherein the ultraviolet light source provides about 254 nm wavelength ultraviolet light.

13. A method as claimed in claim 11 wherein the step of illuminating includes illuminating with a visible light source.

14. A method as claimed in claim 10 wherein the ultraviolet light source is long wave ultraviolet source.

15. A method as claimed in claim 14 wherein the ultraviolet light source provides about 365 nm wavelength ultraviolet light.

16. A method as claimed in claim 14 wherein the step of illuminating includes illuminating with a visible light source.

17. A method as claimed in claim 10 wherein the ultraviolet light source is both a short and a long wave ultraviolet source.

18. A method as claimed in claim 17 also including a visible light source.

19. A method as claimed in claim 10 wherein the step of illuminating includes illuminating with a visible light source.

20. A method of self-diagnostic testing for a digital radiography system, the method comprising the steps of:
    illuminating with a visible light source a scintillator of a digital radiography system including a target area;
    imaging the scintillator with a digital camera of the radiography system, including the target area to form at least one test image;
    comparing the test image to a predetermined reference image; and
    reporting a result of the comparison.

* * * * *